United States Patent
Shahdoostfard et al.

(10) Patent No.: US 12,059,260 B2
(45) Date of Patent: *Aug. 13, 2024

(54) CHANNEL INTEGRITY DETECTION AND RECONSTRUCTION OF ELECTROPHYSIOLOGICAL SIGNALS

(71) Applicant: CARDIOINSIGHT TECHNOLOGIES, INC., Independence, OH (US)

(72) Inventors: Shahabedin Shahdoostfard, Independence, OH (US); Qingguo Zeng, Solon, OH (US); Ping Jia, Solon, OH (US); Brian P. George, Cleveland, OH (US); Kevin Ponziani, Independence, OH (US); Qing Lou, Powell, OH (US); Daniel Varghai, Independence, OH (US); Jeffrey B. Adair, Independence, OH (US)

(73) Assignee: CARDIOINSIGHT TECHNOLOGIES INC., Independence, OH (US)

( * ) Notice: Subject to any disclaimer, the term of this patent is extended or adjusted under 35 U.S.C. 154(b) by 514 days.

This patent is subject to a terminal disclaimer.

(21) Appl. No.: 17/101,629

(22) Filed: Nov. 23, 2020

(65) Prior Publication Data

US 2021/0100466 A1    Apr. 8, 2021

Related U.S. Application Data

(63) Continuation of application No. 15/913,262, filed on Mar. 6, 2018, now Pat. No. 10,874,318.

(51) Int. Cl.
*A61B 5/327*    (2021.01)
*A61B 5/00*    (2006.01)
(Continued)

(52) U.S. Cl.
CPC .............. *A61B 5/327* (2021.01); *A61B 5/282* (2021.01); *A61B 5/30* (2021.01); *A61B 5/316* (2021.01);
(Continued)

(58) Field of Classification Search
CPC ........... A61B 5/327; A61B 5/282; A61B 5/30; A61B 5/316; A61B 5/339; A61B 5/7221; A61B 5/7257; A61B 5/305; A61B 5/367
See application file for complete search history.

(56) References Cited

U.S. PATENT DOCUMENTS

| 4,558,702 A | 12/1985 | Barreras et al. |
| 4,862,897 A | 9/1989 | Eisenberg et al. |

(Continued)

FOREIGN PATENT DOCUMENTS

| CN | 101534708 A | 9/2009 |
| CN | 103417206 A | 12/2013 |

(Continued)

OTHER PUBLICATIONS

Koessler, L. et al.; "Spatial Localization of EEG Electrodes"; Neurophysiology Clinique—Clinical Neurophysiology, Elsevier, Paris, FR, vol. 3, No. 2, Apr. 1, 2007; pp. 97-102, XPO253201869, ISSN: 0987-7053, DOI: 10.1016/J.NEUCLI.2007.03.002 [Retrieved on Apr. 1, 2007].

(Continued)

*Primary Examiner* — Mallika D Fairchild
(74) *Attorney, Agent, or Firm* — Tarolli, Sundheim, Covell & Tummino LLP

(57) ABSTRACT

This disclosure relates to integrated channel integrity detection and to reconstruction of electrophysiological signals. An example system includes a input channels configured to receive respective electrical signals from respective electrodes. An amplifier stage includes a plurality of differential
(Continued)

amplifiers, each of the differential amplifiers being configured to provide an amplifier output signal based on a difference between a respective pair of the electrical signals. Channel detection logic is configured to provide channel data indicating an acceptability of each of the input channels based on an analysis of a common mode rejection of the amplifier output signals.

20 Claims, 10 Drawing Sheets

(51) Int. Cl.
    *A61B 5/282* (2021.01)
    *A61B 5/30* (2021.01)
    *A61B 5/316* (2021.01)
    *A61B 5/339* (2021.01)
(52) U.S. Cl.
    CPC ............ *A61B 5/339* (2021.01); *A61B 5/7221* (2013.01); *A61B 5/7257* (2013.01)

(56) References Cited

U.S. PATENT DOCUMENTS

| | | | |
|---|---|---|---|
| 4,922,920 | A | 5/1990 | Thie et al. |
| 4,974,598 | A | 12/1990 | John |
| 4,979,110 | A | 12/1990 | Albrecht et al. |
| 4,991,587 | A | 2/1991 | Blakeley et al. |
| 4,993,421 | A | 2/1991 | Thornton |
| 5,054,496 | A | 10/1991 | Wen et al. |
| 5,161,539 | A | 11/1992 | Evans et al. |
| 5,307,817 | A | 5/1994 | Guggenbuhl et al. |
| 5,810,740 | A | 9/1998 | Paisner |
| 6,263,235 | B1 | 4/2001 | Kaiser et al. |
| 6,370,423 | B1 | 4/2002 | Guerrero et al. |
| 6,397,845 | B1 | 6/2002 | Burton |
| 2003/0083584 | A1 | 5/2003 | Yonce |
| 2004/0059761 | A1 | 3/2004 | Hively |
| 2006/0095083 | A1 | 5/2006 | Zhang et al. |
| 2007/0232948 | A1 | 10/2007 | Stadler et al. |
| 2008/0269813 | A1 | 10/2008 | Greenhut et al. |
| 2010/0007413 | A1* | 1/2010 | Herleikson ............ A61B 5/276 |
| | | | 330/124 R |
| 2010/0094155 | A1 | 4/2010 | Prichep |
| 2011/0043217 | A1 | 2/2011 | Tszampazis et al. |
| 2011/0282180 | A1 | 11/2011 | Goldkuhl et al. |
| 2011/0319777 | A1 | 12/2011 | Mehrotra et al. |
| 2013/0131529 | A1* | 5/2013 | Jia .......................... A61B 5/333 |
| | | | 600/509 |
| 2013/0304407 | A1* | 11/2013 | George ................ A61B 5/7203 |
| | | | 702/72 |
| 2015/0241505 | A1 | 8/2015 | Freeman et al. |
| 2015/0327815 | A1* | 11/2015 | Hwang ................ A61B 5/7225 |
| | | | 600/547 |
| 2016/0116516 | A1 | 4/2016 | Xia et al. |
| 2017/0219509 | A1 | 8/2017 | Bakalos et al. |

FOREIGN PATENT DOCUMENTS

| | | |
|---|---|---|
| CN | 103829941 A | 6/2014 |
| CN | 107049311 A | 8/2017 |
| JP | 3423324 B2 | 7/2003 |
| WO | 2004008373 | 1/2004 |
| WO | 2004034886 | 4/2004 |
| WO | 2007146864 | 12/2007 |
| WO | 2008034886 A1 | 3/2008 |

OTHER PUBLICATIONS

Gronlund, C., et al.; "On-Line Signal Quality Estimation of Multichannel Surface Electromyograms"; Medical and Biological Engineering and Computing, Springer Heildelberg, DE, vol. 43, No. 3, May 1, 2005; pp. 357-364, XP001508011; ISSN: 0140-0118, DOI: 10.1007/BF02345813.

Applicant: CardioInsight Technologies Inc.; "Channel Integrity Detection and Reconstruction of Electrophysiological Signals"; European Application No. 19764211.9; Extended European Search Report; Mailed Oct. 22, 2021; 8 pgs.

Chinese Application No. 201980009082.7; Machine Translated First Chinese Office Action Dated Sep. 22, 202318 pgs.

Applicant: CardioInsight Technologies Inc.; European Application No. 19764211.9; EP Office Communication; dated Mar. 20, 2024; 5 pgs.

* cited by examiner $$\begin{bmatrix} 1 & f(x_1-y_1) & \cdots & f(x_1-y_M) \\ 1 & f(x_2-y_1) & \cdots & f(x_2-y_M) \\ \vdots & \vdots & & \vdots \\ 1 & f(x_k-y_1) & \cdots & f(x_k-y_M) \\ \vdots & \vdots & & \vdots \\ 1 & f(x_N-y_1) & \cdots & f(x_N-y_M) \\ 0 & \dfrac{\partial f(x_1-y_1)}{\partial \vec{n}} & \cdots & \dfrac{\partial f(x_1-y_M)}{\partial \vec{n}} \\ 0 & \dfrac{\partial f(x_2-y_1)}{\partial \vec{n}} & \cdots & \dfrac{\partial f(x_2-y_M)}{\partial \vec{n}} \\ \vdots & \vdots & & \vdots \\ 0 & \dfrac{\partial f(x_N-y_1)}{\partial \vec{n}} & \cdots & \dfrac{\partial f(x_N-y_M)}{\partial \vec{n}} \end{bmatrix} \begin{bmatrix} a_0 \\ a_1 \\ \vdots \\ \vdots \\ \vdots \\ a_M \end{bmatrix} = \begin{bmatrix} u(x_1) \\ u(x_2) \\ \vdots \\ u(x_k) \\ \vdots \\ u(x_N) \\ 0 \\ 0 \\ \vdots \\ \vdots \\ 0 \end{bmatrix}$$

FIG. 13

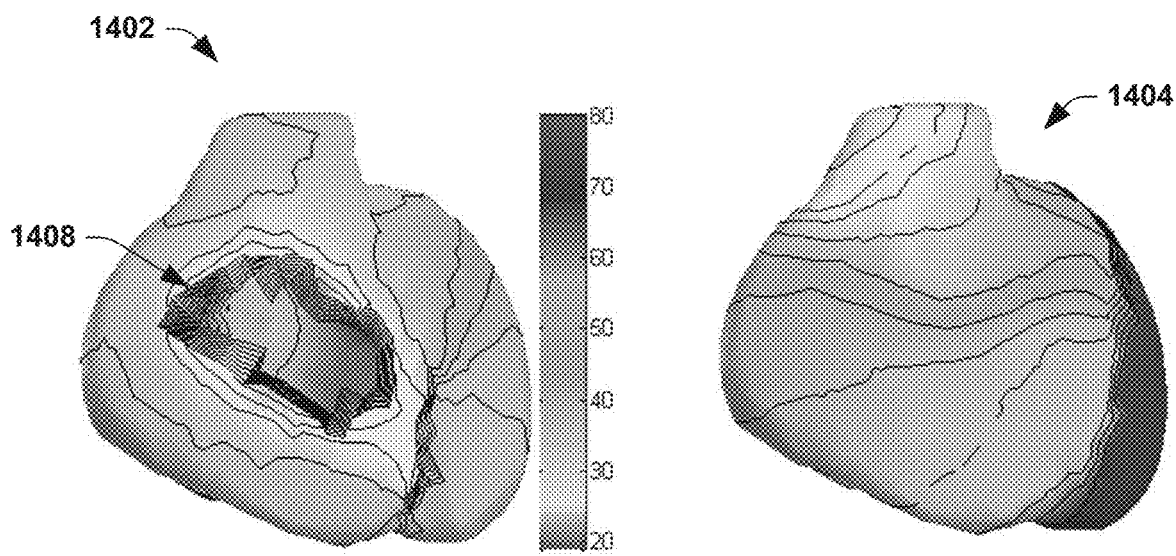

FIG. 14A  FIG. 14B

CHANNEL INTEGRITY DETECTION AND RECONSTRUCTION OF ELECTROPHYSIOLOGICAL SIGNALS

CROSS-REFERENCE TO RELATED APPLICATION

This application is a continuation of U.S. non-provisional patent application Ser. No. 15/913,262 filed on Mar. 6, 2018, and entitled CHANNEL INTEGRITY DETECTION AND RECONSTRUCTION OF ELECTROPHYSIOLOGICAL SIGNALS, which is incorporated herein by reference in its entirety.

TECHNICAL FIELD

This disclosure relates to integrated channel integrity detection and to reconstruction of electrophysiological signals.

BACKGROUND

Body surface electrical activity (e.g., electrophysiological signals) can be sensed by an arrangement of electrodes. The sensed signals can be processed for a variety of applications, such as for body surface mapping or reconstruction of onto a surface such as for electrocardiographic mapping. Since these and other processing methods can depend on body surface potential data, the presence or absence of quality signals can affect outputs generated based on signal processing.

SUMMARY

In one example, a system includes a plurality of input channels configured to receive respective electrical signals from a set of electrodes. An amplifier stage includes a plurality of differential amplifiers, each of the differential amplifiers being configured to provide an amplifier output signal based on a difference between a respective pair of the electrical signals. Channel detection logic is configured to provide channel data indicating an acceptability of each of the plurality of input channels based on an analysis of a common mode rejection of the amplifier output signals.

In another example, a method includes receiving, via a plurality of input channels, respective input electrical signals sensed by a set of electrodes. The method also includes amplifying, via a plurality of differential amplifiers, a difference between respective pairs of the input electrical signals and providing an amplified output signal corresponding to the difference. The method also includes analyzing the amplified output signals to determine a relative impedance associated with each electrode in the set of electrodes. The method also includes generating channel data to specify an acceptability or unacceptability for each of the plurality of input channels based on the analyzing.

As another example, a system includes a plurality of electrodes configured to sense electrical signals across a body surface of a patient. A processor executes machine readable instructions stored in one or more non-transitory media. The instructions are configured to compute a transformation matrix based on at least one boundary condition and geometry data associated with the plurality of electrodes. The instructions are further configured to modify the transformation matrix based on bad channel data specifying that one or more of a plurality of input channels, which receive electrical signals from the plurality of electrodes, are unacceptable while retaining geometry information for each of the plurality of electrodes. Reconstructed electrical signals are estimated on a cardiac envelope based on the modified transformation matrix and the electrical signals from the plurality of electrodes As another example, a method includes storing geometry data and electrical signal data associated with a plurality of electrodes arranged for sensing body surface electrical signals. The method also includes computing a transformation matrix based on at least one boundary condition and geometry data associated with the electrodes. The method also includes modifying the transformation matrix based on bad channel data specifying that a connection of one or more of a plurality of electrodes with the body surface is unacceptable while retaining location information for each of the plurality of channels and providing a modified transformation matrix. The method also includes estimating the reconstructed electrical signals on the cardiac envelope based on the modified transformation matrix and the electrical signals from the plurality of electrodes.

BRIEF DESCRIPTION OF THE DRAWINGS

FIG. 13 depicts an example of an adjusted transformation matrix.

FIGS. 14A and 14B depict examples of graphical maps generated from electrical signals for a normal sinus rhythm reconstructed with and without including signal information for bad channels.

DETAILED DESCRIPTION

Figure 1:
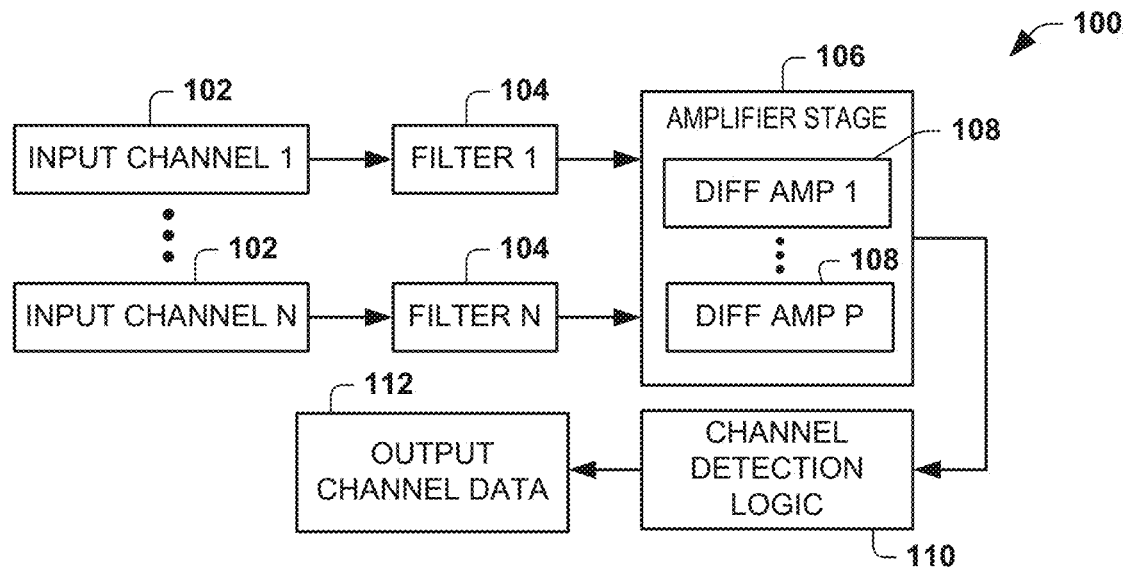
FIG. 1 depicts an example of a system to determine integrity of input channels.

This disclosure relates to systems and methods to determine channel integrity for a plurality of input channels. Each of the input channels can carry sensed electrical signals from a respective electrode. Channels identified as being unacceptable (or not classified as being acceptable) may be utilized in further processing and analysis. As an example, the further processing and analysis can include reconstructing signals on a body surface based upon the input channel data (e.g., via an inverse solution). Additional calculations can be performed on the reconstructed data, such as to generate one or more graphical maps and characterize the reconstructed data.

As an example, the channel integrity systems and methods may be implemented to provide channel data that identifies which channels may include signal outside of expected operating parameters, such as due to electrodes failing to contact a target or otherwise fail to establish acceptable contact with the target. For example, differential amplifiers are configured to provide amplifier output signals based on a difference between respective pairs of the electrical input signals. The signals may be filtered so as to include a common signal of the system, such as a line interference (noise) signal. The amplified signals are further processed to analyze the amplifier output signals to ascertain a common mode rejection of the electrodes. A relative impedance of the input channels may be implied from the common mode rejection performance of the input channels, such as by detecting that a given channel has a higher voltage than one or more other channels. The relative impedance may be utilized to derive the channel data specifying an acceptability of contact between each electrode and the target. Unlike some existing approaches, the systems and methods disclosed herein can specify both which electrodes are in contact with the target and, among those electrodes that are in contact, which electrodes are not establishing an acceptable contact. In some systems, little or no modifications to existing hardware. By removing bad or missing channels from further processing, the approach can not only achieve improved accuracy in such further processing and analysis but also improves the system's workflow, such as by reducing preprocessing time.

This disclosure also relates to systems and methods to reconstruct electrical activity on a surface of interest within a patient's body based on signals measured on an outer surface of the patient's body (e.g., via electrodes). For example, systems and methods are disclosed to implement an inverse method calculation by reconstructing electrical signals on a surface (e.g., cardiac envelope) within a patient's body based on the measured electrical signals and geometry data representing geometry of the set of electrodes relative to anatomy (e.g., in three-dimensional space). The inverse reconstruction may include calculating a transformation matrix based on at least one boundary condition and the geometry data. The boundary condition can vary depending on the inverse reconstruction method being implemented. Any channel for which an electrode does not adequately contact the target is identified and stored in channel data. The channel data may be generated according to any channel integrity methods disclosed herein, manual methods as well as other approaches. The transformation matrix that is used in the inverse reconstruction is adjusted based on the channel data to provide a modified transformation matrix. As one example, this may include removing electrical signal data for each bad channel from the transformation matrix while still retaining geometry information for all channels including bad channels. As another example, the adjustment may include replacing the electrical signal information for each bad channel in the transformation matrix with unknown variables for such channels. The modified transformation matrix thus may be employed with the input electrical signals to compute the reconstructed electrical signals on the cardiac envelope. The systems and methods disclosed herein for reconstructing the electrical signals on the surface thus may achieve improved accuracy over other approaches (e.g., that use interpolated signals for channels).

FIG. 1 depicts an example of a channel integrity detection system 100 that can be utilized to provide an indication of channel integrity for a plurality of input channels. For example, the channel integrity may indicate whether physical contact between an electrode, which provides a sensor signal, and a target is acceptable or unacceptable (e.g., a missing or bad connection) for further processing of the sensor signal. The channel integrity system 100 can be implemented as hardware (e.g., circuitry and/or devices), software (e.g., a non-transitory medium having machine readable instructions) or a combination of hardware and software.

The system 100 includes a plurality of N input channels 102 configured to receive respective electrical signals from a set of electrodes, where N is a positive integer greater than two. In some examples, the input channels 102 provide electrical signals sensed by sensing electrodes that are placed on a body surface of the patient, which can be an internal body surface (e.g., invasive) or an external body surface (e.g., non-invasive) or a combination thereof. In many examples herein, the body surface is described as the patient's thorax, such as for sensing cardiac electrical activity. In other examples, other body surfaces may be used, such as the head or other parts of the body according to the purpose for which electrical activity is being sensed. In some examples, the input channels can correspond to pre-filtered input data, such as prior to implementing line-filtering and other signal processing (e.g., offset correction, analog-to-digital conversion and the like) to remove selected noise components from the respective input channels. Each of the input channels 102 may thus include power line interference signals, corresponding to a common mode signal for each channel and the system 100.

The input channels 102 provide respective electrical signals to an amplifier stage 106. In some examples, a filter 104 is coupled between each input channel and a respective input amplifier stage. For instance, each filter 104 is configured (e.g., as a low pass, anti-aliasing filter) that attenuates or blocks frequencies higher than a predetermined cutoff frequency. Each filter 104 provides a filtered signal having a frequency below the cutoff frequency such that the filtered signal includes a common mode signal. The filters 104 are coupled to provide their filtered signals to one or more inputs of the amplifier stage 106. By utilizing the line noise signal as a common mode signal for the system 100, no additional input signals need to be injected into the system to detect channel integrity, as disclosed herein.

The amplifier stage 106 includes a plurality of differential amplifiers 108, each configured to provide an amplified output signal based on a difference between a respective pair of input electrical signals from respective input channels. For example, each respective pair of input channels may be connected to inputs of one or more differential amplifiers. In an example, the filtered signal may be directly connected to the inputs of the differential amplifiers. In another example the filtered outputs may be connected to the inputs of the differential amplifiers via other circuitry (e.g., a switching network—not shown) that routes the filtered input channel signals to the amplifier inputs. In some examples, a switching network may be used to selectively connect the filters 104 into the channel paths (between the input channels and amplifier stage) for performing channel integrity functions and out of the channel paths for implementing other signal processing functions.

The system also includes channel detection logic 110 configured to provide channel data 112 indicating an acceptability or unacceptability of each of the plurality of input channels. As disclosed herein, the channel detection logic 110 can analyze a common mode rejection performance based on the amplifier output signals. By way of example, since the electrodes for each channel are almost identical, a common range for electrode impedances are expected assuming connection quality for each electrode to the target is proper (e.g., good electrical contact between the electrode and the target). Therefore, a common mode signal for each channel, corresponding existing power line noise, will propagate through the system as a common mode signal and be present at the amplifier inputs.

In some examples of high-density electrode measurement systems, the set of electrodes includes a reference electrode and a plurality of other electrodes. In this example, each respective pair of electrical signals, which are provided to a given differential amplifier 108, may include a signal from the reference electrode and a signal from another of the plurality of other electrodes. That is, each of the plurality of differential amplifiers 108 includes a first input coupled to receive a reference signal from the reference electrode and a second input coupled to receive the electrical signal (e.g., filtered signal) from one of the plurality of other electrodes. The amplifier output signal of each of the plurality of differential amplifiers thus provides an indication of common mode signal performance between signals from the reference electrode and the respective other electrode. The indication of common mode signal performance provided by each of the differential amplifiers further may be evaluated to determine a relative impedance of each electrode. For instance, high electrode impedances are either due to disconnected electrodes or non-properly connected electrodes.

As an example the channel detection logic 110 may be configured (e.g., hardware and/or software) to implement signal processing to determine a channel integrity state for each channel. For example, the channel detection logic 110 implements a fast Fourier transform to convert the output of each differential amplifier to frequency domain data having an amplitude value representing the power at different frequencies, which can include the frequency of the common mode signal (e.g., power line noise). A frequency analyzer can apply a threshold to the frequency domain data at the common mode frequency to provide the channel data 112 for the plurality of input channels.

The channel data 112 thus can identify a set of one or more nodes having low integrity (e.g., data specifying whether channels as bad). The output channel data 112 can be provided in terms of a list of nodes indexed according to input channel that can be provided to subsequent processing blocks so that the corresponding data for a given channel is processed in a particular manner or not utilized in subsequent signal processing and data analysis. As an example, the output channel data 112 can be provided in terms of channel integrity that is considered bad, good, or can identify both bad and good channels. In some examples, a logic value (e.g., 0 or 1) can be used to specify if a channel is good or bad. The channel integrity values for a given channel may be fixed or in some examples might change over time, such as in response to changing the extent of contact between a given electrode and the target surface. The system thus may provide the channel data 112 without any requiring hardware modifications as well as be implemented with reduced processing time compared to existing approaches (e.g., milliseconds versus seconds).

In some examples, spikes or other signals that may affect the FFT amplitude at the common mode frequency, are detected and removed from the input electrical signals for each input channel 102. For example, pacing spikes may be applied to one or more locations on the heart. The spikes are received differently across the input channels yet still contribute to the FFT amplitude at the common mode frequency. Accordingly, such spikes may be detected for each input channel, for example using a wavelet based method, and be removed from each input signal using spline interpolation (e.g., a piece-wise monotonic cubic spline interpolation). In this way, spikes or other signals may be excluded from the subsequent signal processing, including the power line noise estimation for each channel.

Figure 2:
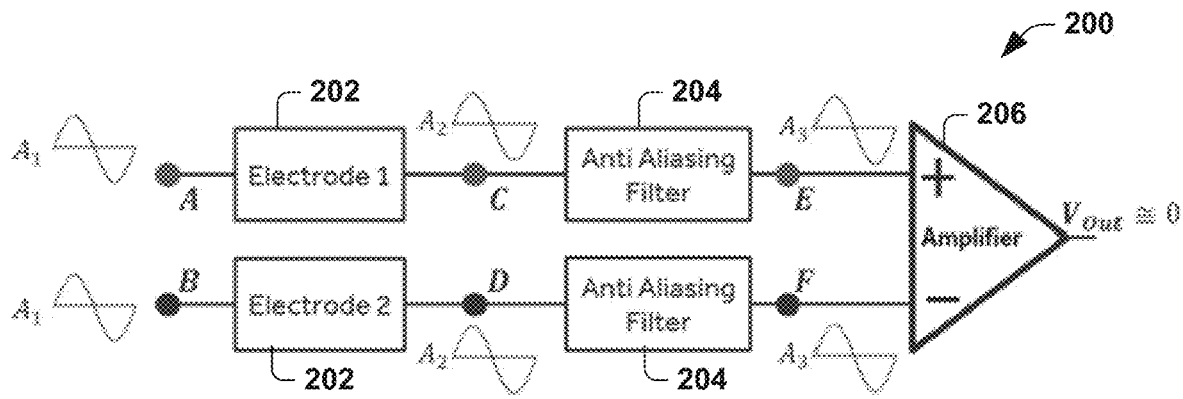
FIG. 2 depicts a block diagram of part of the system of FIG. 1 for processing a pair of input channels exhibiting a first common mode rejection performance.
Figure 3:
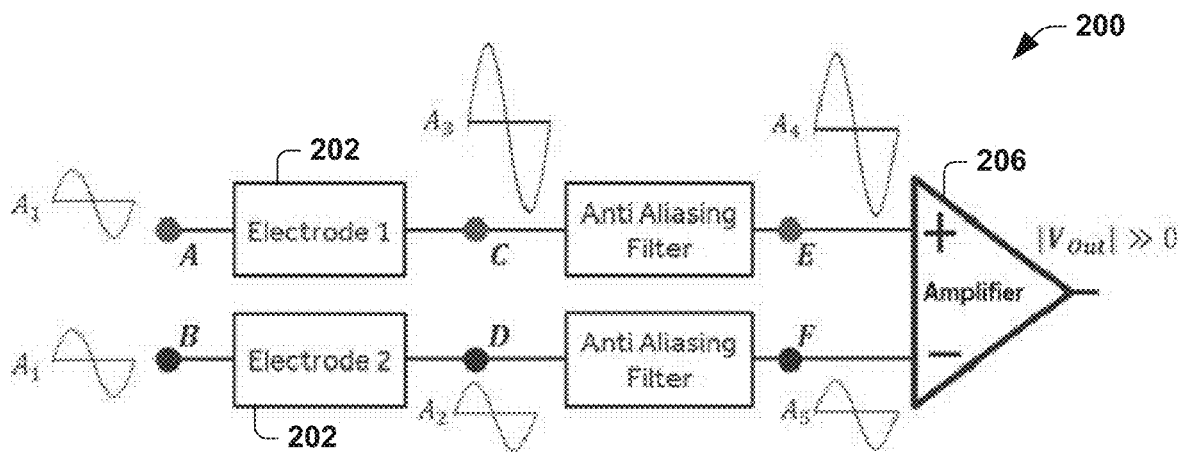
FIG. 3 depicts a block diagram of part of the system of FIG. 1 for processing a pair of input channels exhibiting a second common mode rejection performance.

FIGS. 2 and 3 depict example front end hardware architectures that may be utilized for capturing information related to common mode rejection associated with a pair of input channels. The examples of FIGS. 2 and 3 depict front end processing for a pair of electrodes (demonstrated as electrodes 1 and 2) 202 that receives a common input signal at A and B, demonstrated as $A_1$. In these examples, the input signals $A_1$ at A and B correspond to a common mode signal, such as a power line noise signal that may be present in any body surface measurement system. The common mode signal thus has a frequency corresponding to the line frequency, which may vary according to location. For example, in the United States, power line noise has a frequency of about 60 Hz, whereas in Europe, power line noise has a frequency of about 50 Hz. Thus, in some examples, filter operation of the system may be switched to depending on where it is being utilized or a default value used to pass both frequencies. This may be done by automatically detecting the frequency of the power line signal or in response to a user input selecting the appropriate operating parameter according to the input power source.

In the example of FIG. 2, each of the electrodes 202 is considered to exhibit common mode behavior with being properly connected to receive the signal $A_1$ at inputs A and B of the target. Thus, the signals between the electrodes 202 and remaining circuitry 204 and 206, demonstrated at nodes C and D, correspond to the common mode signals. Anti-aliasing filters 204 filter the input signals at nodes C and D to pass low frequency components including the line noise signals. Thus, each of the filters 204 provides filtered signals in which the high frequency components have been removed. The filtered signals at nodes E and F corresponding to inputs of the differential amplifier 206. Node E is connected to a non-inverting input and node F is connected to the inverting input of amplifier 206. In the example of FIG. 2, the output of amplifier 206 is approximately zero based on the common mode signals at E and F being approximately equal in response to the common node signals at inputs A and B propagating through the system as a common mode signal thus resulting in good common mode rejection as expected.

The example of FIG. 3 corresponds to a scenario in which one of the electrodes 202 is not properly connected (e.g., inadequate or no contact with the target). Specifically, in the example of FIG. 3, electrode 2 is properly connected to the target but electrode 1 is not. Therefore, due to its increased input impedance relative to electrode 2, the signal provided by electrode 1 at node C has a higher amplitude than the signal at D provided by electrode 2. Based on the inadequate contact of electrode 1 compared to electrode 2, the common mode signal at the differential inputs A and B will not propagate symmetrically through the system to the amplifier inputs at E and F. As a result, the amplified output signal by an amplifier 206 is greater than zero corresponding to poor common mode rejection performance.

The examples of FIGS. 2 and 3 are applicable to the multi-input channel example of FIG. 1, in which the differential amplifier is 108 each receives a respective different pair of filtered signals and thus provides differential amplified outputs reflecting the common mode rejection for each respective input channel pair. By comparing the power of common mode signals at the output of each respective input channel pair and comparing such power to the power of adjacent pairs, channel detection logic 110 can determine whether one or more bad electrodes exist. By implementing additional comparisons between electrode signals and/or other information from the set of channels, the channel detection logic 110 further can detect and identify which (if any) electrodes exhibit electrode impedance values corresponding to improper connection criteria.

Figure 4:
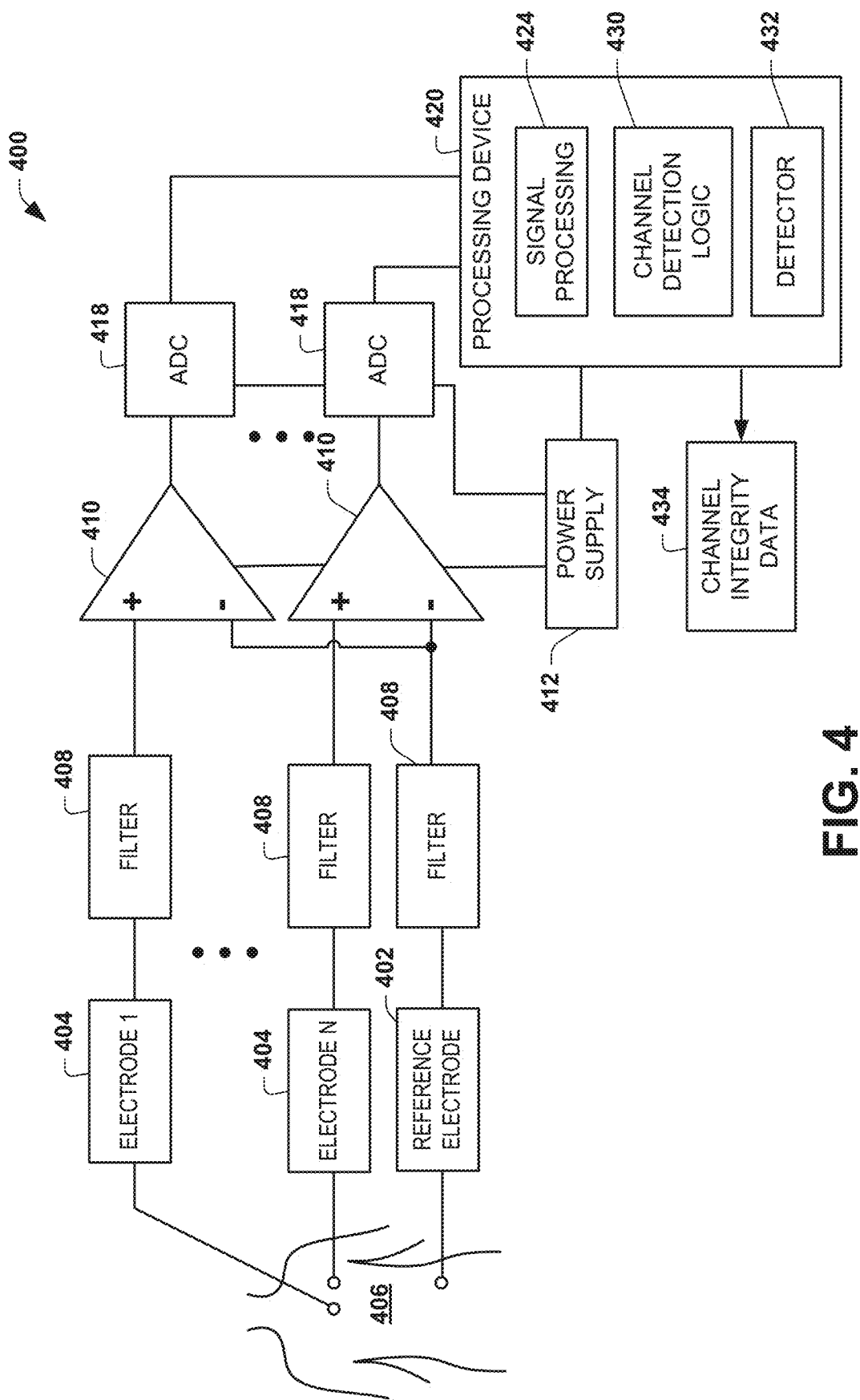
FIG. 4 depicts an example of another system for determining integrity for a plurality of electrodes.

FIG. 4 depicts another example of another system 400 for determining integrity for a plurality of electrodes. In this example, one of the electrodes 402 is demonstrated as a reference electrode and remaining electrodes 404 are positioned across the body surface. Each of the electrodes may be identical in configuration and designed to contact (e.g., directly or indirectly through an electrically conductive gel or other contact agent) the body surface for sensing electrical activity. There can be any number of electrodes 1 through N, where N is a positive integer. For ease of illustration, the electrodes 404 and 402 are depicted schematically disposed on a body 406. There can be any number and arrangement of electrodes 402 and 404 on the body surface depending upon the function and purpose of the sensing. For example, the electrodes can be used to sense other electrophysiological conditions, such as for use in an electrode encephalogram, electromyogram or the like.

In the example of FIG. 4, the arrangement of the processing circuitry is similar to as disclosed with respect to FIGS. 1-3. The system 400 includes a filter 408 that is coupled between each of the electrodes 402, 404 and an input of an amplifier 410. In this particular example, each of the electrodes 404 is coupled through its respective filter 408 to a non-inverting input of the differential amplifier. The reference electrode 402 is coupled to an inverting input of the differential amplifier via its filter 408. As disclosed herein, each of the filters 408 operates as a anti aliasing filter to remove unwanted signal components such as high frequencies above a known common mode signal such as power line interference.

For example, one or more power supplies 412 may be coupled to supply electrical energy to the system 400, including directly to active circuit components, such as can include the amplifiers 410, analog to digital converters 418 and a processing device 420. For example, the power supply may be connected to a source of AC power (e.g., a power outlet) and supply DC or AC power to various components in the system 400. Thus, the connection of the power supply to the AC power source results in power line noise on the electrical signals detected by each of the electrodes 402 and 404. Additionally or alternatively, line noise may also be provided from electrical devices and equipment coupled to the system 400 (directly or indirectly) or otherwise from devices operating the surrounding environment, such as lights, display devices other equipment (e.g., health monitoring equipment). While such power line noise is filtered out via line filters to remove noise from the sensed signals for further processing, the signals of interest in the examples disclosed herein include the line noise as a common mode signal.

The differential output from each of the amplifiers 410 are provided as analog outputs to the ADC 418. The ADC in turn converts the analog signal to a corresponding digital version and provides the digital signal to an input of the processing device 420. The processing device 420 is configured (e.g., a digital signal processor, field programmable gate array, computer or other processing apparatus) to implement signal processing 424 and channel detection logic 430. The signal processing 424 may perform signal conversion, sampling and other functions. The channel detection logic 430 analyzes the processed signals to determine a common mode rejection for each of the differential amplifiers, which is supplied via the ADC blocks 418. The determined common mode rejection for each of the differential amplifiers is evaluated and utilized by the detector 432 to determine channel integrity for each of the respective electrodes 402 and 404.

The processing device 420 outputs channel integrity data 434. For example, the channel integrity data 434 can indicate whether or not each of the electrodes 404 is connected to the target, demonstrated as the surface of the body 406. In some examples, channel integrity data 434 can also indicate whether or not the reference electrode(s) 402 is connected to the target such as based on implementing additional comparisons and/or logic. In another example, manual confirmation (e.g., via user input) may be used to specify the validity of the connection of the reference electrode. Additionally or alternatively, the channel integrity data 434 may similarly specify whether the connection between the electrodes 402, 404 and the body surface is unacceptable for processing purposes. This information can be stored as part of the channel integrity data in a data record for each of the respective electrodes 402 and 404. The channel integrity data 434 thus may be stored in memory for subsequent processing and display.

Figure 5:
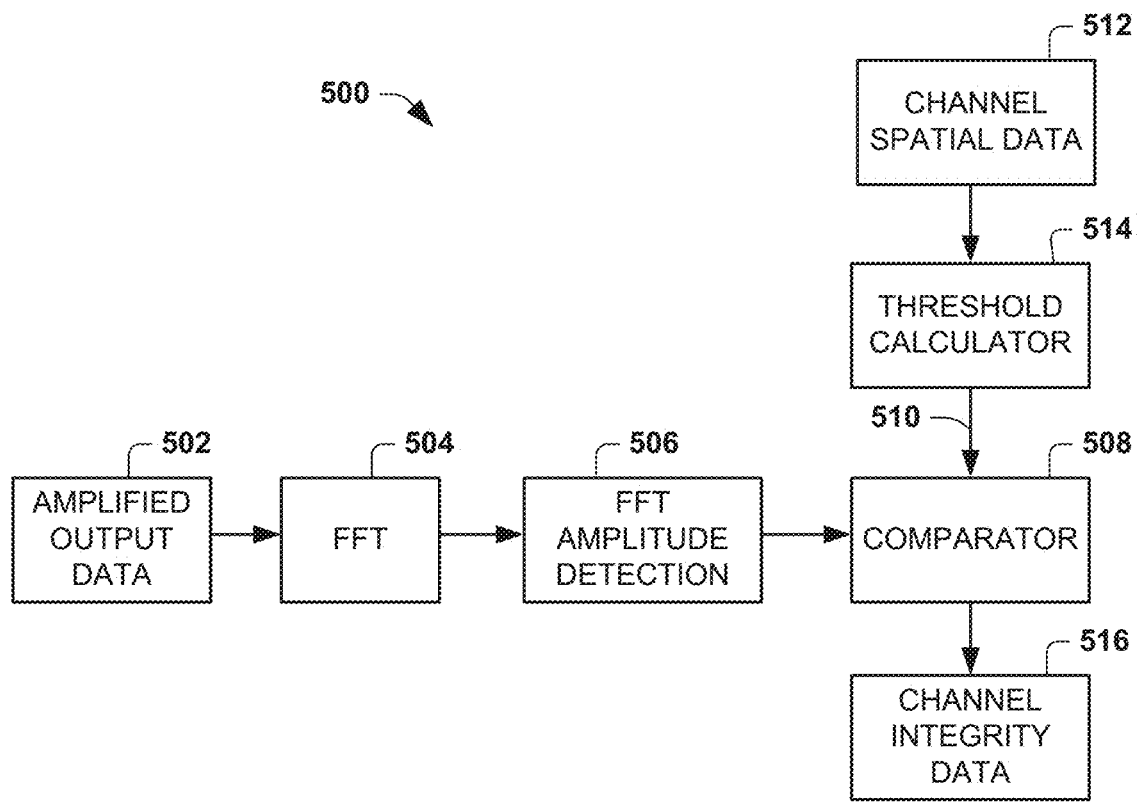
FIG. 5 is a block diagram depicting an example of channel detection logic.

FIG. 5 depicts an example of channel detection logic 500, such as may correspond to channel detection logic 110 or 430. The channel detection logic 500 receives amplified output data 502, such as digital data provided by an ADC (ADC 418) corresponding to a digital version of the amplified output provided by differential amplifiers disclosed herein. For example, the amplified output data 502 represents relative common mode signal performance or common mode rejection performance between a pair of input channels. The amplified output data 502 can vary over time, such as may include one or more time intervals.

A fast Fourier transform (FFT) 504 converts the amplified output data 502 from the time domain to a corresponding frequency domain representation. The frequency domain data thus represents power of frequency content that is present in signals represented in the amplified output data 502. FFT amplitude detection function 506 detects an amplitude of power at a predetermined frequency of interest. As mentioned, the frequency may include a frequency of the common mode signal, such as corresponding to the power line interference signal (e.g., 50 Hz or 60 Hz).

A comparator 508 compares the detected power amplitude at the predetermined frequency with a corresponding threshold 510. The threshold 510 may be fixed or may be calculated based on analysis of other common mode signals in the system. For example, channel data for a plurality of channels may be stored as channel spatial data 512. For example, the channel spatial data 512 may be derived from FFT amplitude detected signals (e.g., from 506) for a group of spatially relevant electrodes. For example, the set of electrodes arranged on the body surface may be grouped into two or more proper subsets of electrodes for each of a plurality of corresponding spatial zones. Each of the spatial zones may include a subset of electrodes, and the signals for each group of electrodes may be evaluated (e.g., over one or more time intervals) to provide common mode signal characteristics for the electrodes in each respective zone. As an example, the FFT amplitude detected signals for each channel in a given zone may be processed to determine mean common mode power (or other statistical information) for each zone channels. A threshold calculator 514 thus may calculate a corresponding threshold for a given zone as a function of the mean common mode power (e.g., as a percentage or other portion of such power) for the given zone. Thus, each zone may have a corresponding zonal threshold. In some examples, a global threshold may be also calculated for the entire set (or a selected superset) of the electrodes. Where both global and zonal thresholds are used, for each zone, the lower of the zonal threshold and the global threshold can be utilized as the threshold 510. The comparator thus may compare the threshold 510 with the FFT amplitude provided by FFT amplitude detection block 506 to provide corresponding channel integrity data 516 for each of the channels.

Figure 6:
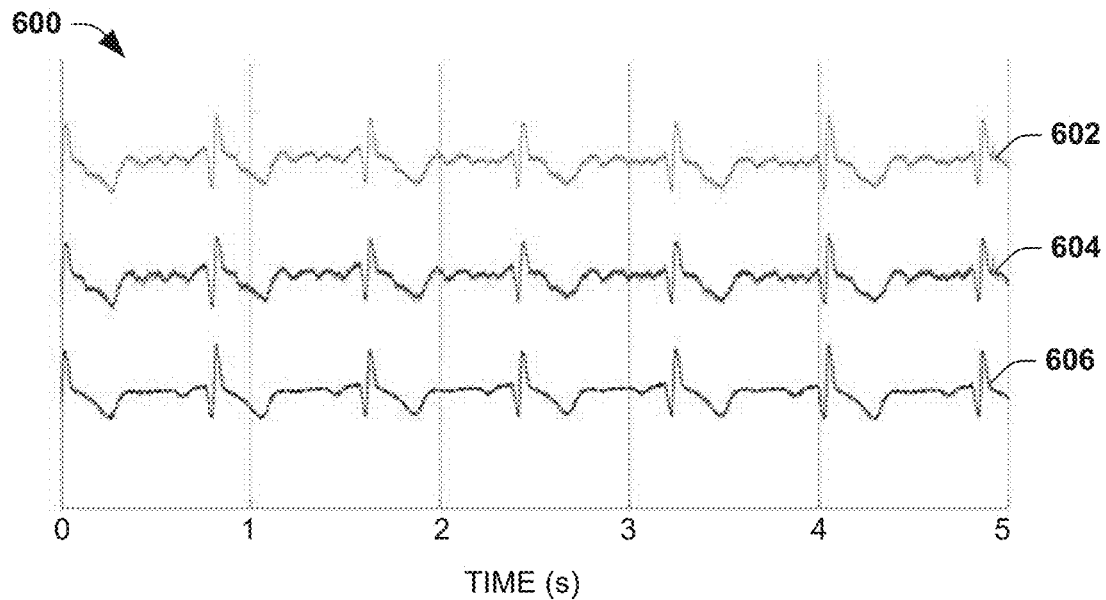
FIG. 6 is an example of waveforms in the example system of FIG. 5.
Figure 7:
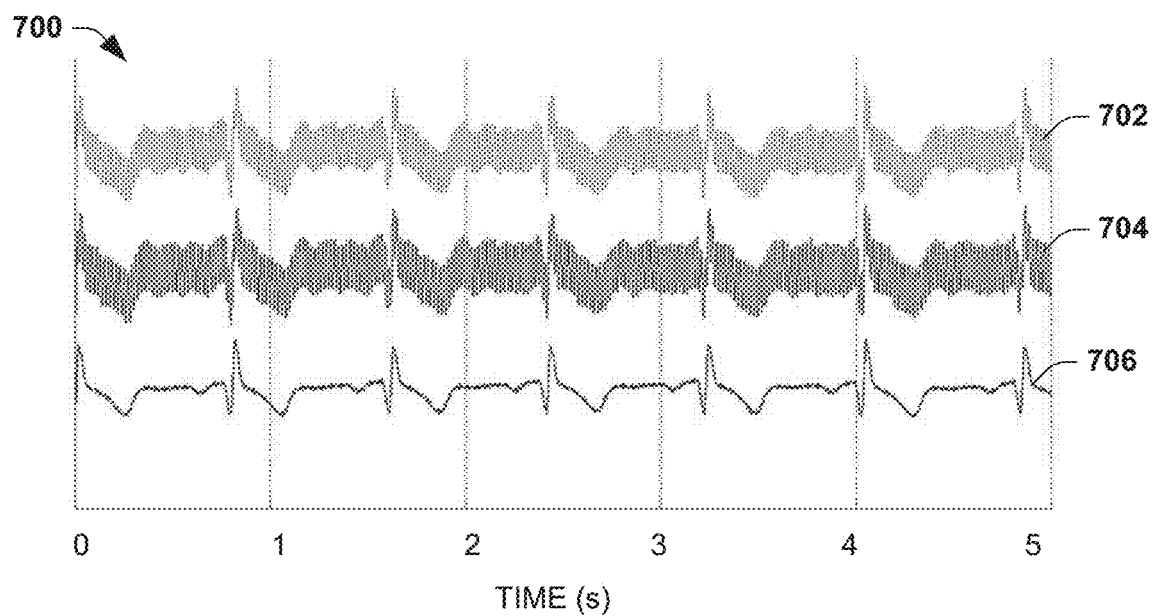
FIG. 7 is an example of other waveforms in the example system of FIG. 5.

FIGS. 6 and 7 illustrate examples of waveforms for use in demonstrating systems and methods herein. FIG. 6 depicts an example of a graph 600 that includes a plurality of waveforms 602, 604 and 606. In the example of FIG. 6, each of the waveforms 602, 604 and 606 corresponds to signals following a line filter in which power line interference (e.g., from the power supply 412 in FIG. 4) has been removed. Accordingly, each of the waveforms 602, 604 and 606 would tend to appear as acceptable input channels according to some existing channel integrity methods, and thus originate with proper electrode connections.

In the example of FIG. 7, the same signals are examined before the line filter such as corresponding to the inputs to the differential amplifiers disclosed herein. In this example, waveforms 702 and 704 demonstrate line interference noise due to high electrode impedance and poor common mode rejection performance. The waveform 706 demonstrates a properly connected electrode with respect to its target surface, corresponding to a low impedance and a good connection.

Figure 8:
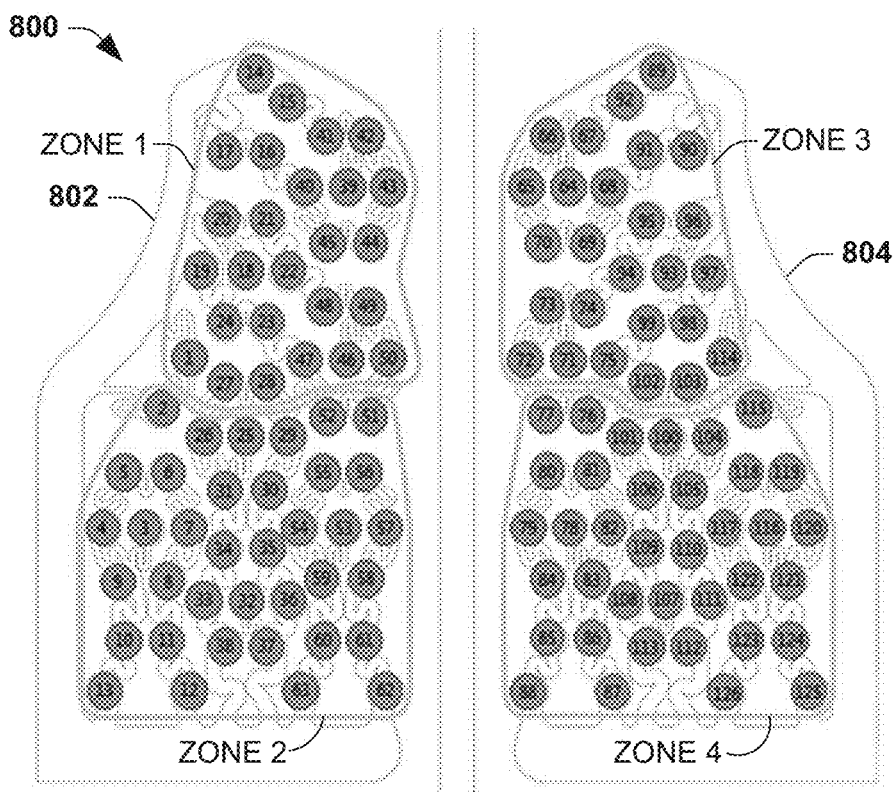
FIGS. 8 and 9 depict examples of a set of electrodes divided into zones.
Figure 9:
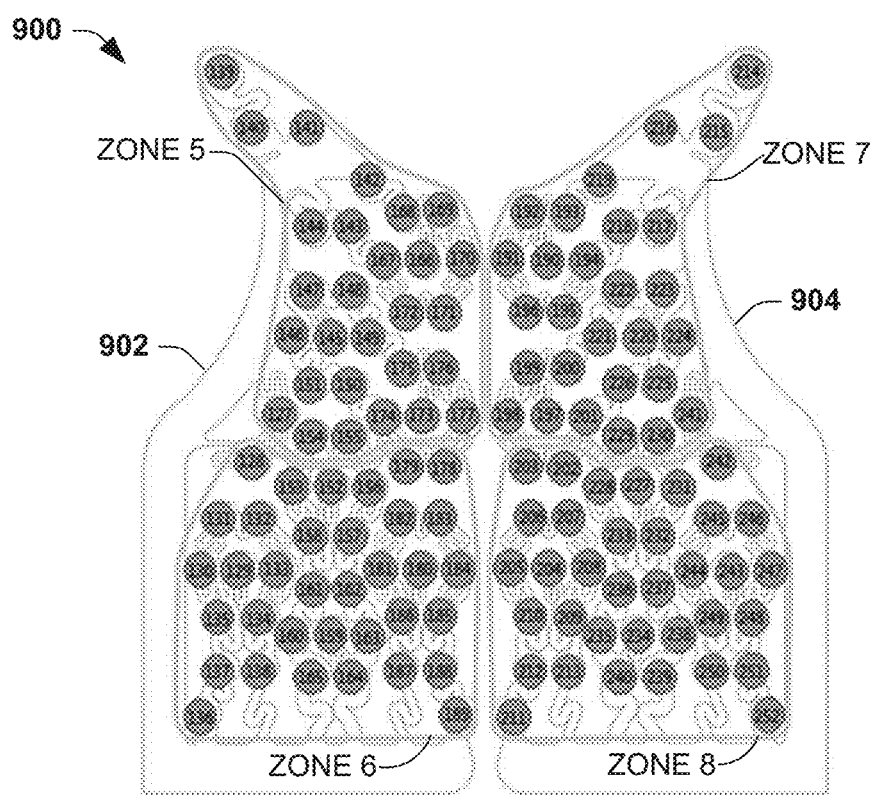

FIGS. 8 and 9 depict different electrode apparatuses 800 and 900 that include electrodes for sensing body surface electrical activity. In the example of FIG. 8, the electrode apparatus 800 includes two portions 802 and 804 that each includes a plurality of electrodes distributed on a contact surface. For instance, the portions 802 and 804 may be part of garment or patch that is configured for placement on an anterior portion of the thorax. As one example, the electrode apparatuses 800 and 900 may be utilized in combination as a sensor array of the type as shown and described in U.S. Pat. No. 9,655,561, which was filed Dec. 22, 2011, or in International patent application No. PCT/US2009/063803, which was filed Nov. 10, 2009, each of which applications is incorporated herein by reference. This non-invasive sensor array corresponds to one example of a full complement of sensors for the patient's thorax. As another example, the electrode apparatus 800, 900 can include an application-specific arrangement of electrodes corresponding to a single sensing zone or multiple discrete sensing zones, such as disclosed in U.S. Pat. No. 9,549,683, which was filed Oct. 12, 2012, and is incorporated herein by reference. Additionally or alternatively, the electrode apparatuses 800 and 900 can include arrangements of electrodes for sensing electrical activity on other body surfaces or invasive sensors that can be inserted into the patient's body.

As shown in FIG. 8, each of the electrodes is grouped into respective zones, demonstrated as zone 1, zone 2, and zone 3 and zone 4. Similarly, in the example of FIG. 9, the electrode apparatus 900 includes portions 902 and 904 that each includes a plurality of electrodes distributed on a contact surface thereof, such as configured for placement on posterior of the thorax. Additionally, each of the electrodes is grouped into respective zones, demonstrated as zone 5, zone 6, and zone 7 and zone 8.

The channel integrity systems and methods disclosed herein thus may analyze the electrodes in each respective zone separately for purposes of determining channel integrity, such as the acceptability of electrode connections. Additionally, in some examples, a separate reference electrode may be utilized for each of the respective zones. In this way, the channel integrity systems and methods can be applied in spatially localized zones to accommodate potential variations in the common mode signals that may be associated with each respective zone.

Figure 10:
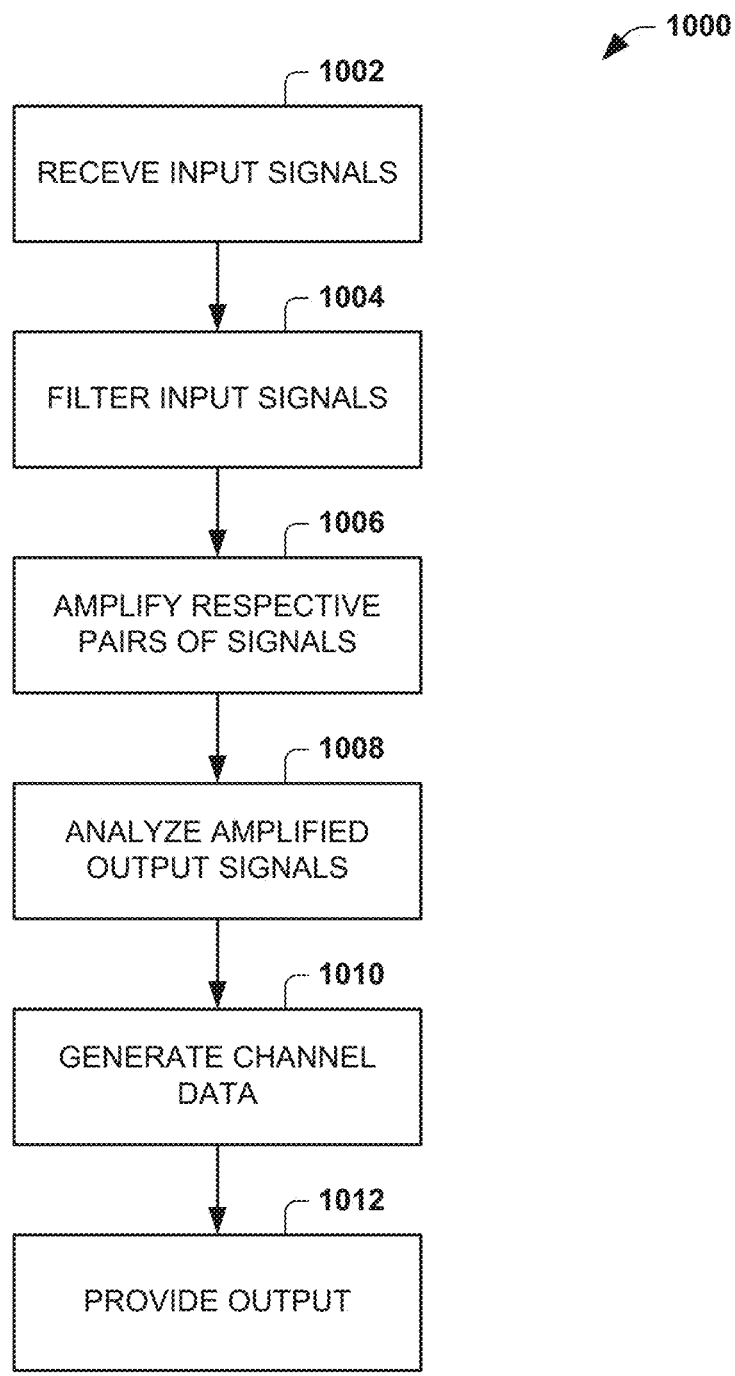
FIG. 10 is a flow diagram depicting an example of method for determining an acceptability or unacceptability for a plurality of input channels.

FIG. 10 is a flow diagram depicting an example of method 1000 for determining an acceptability or unacceptability for a plurality of input channels. Portions of the method 1000 may be implemented by hardware, software or a combination of hardware and software, such as disclosed herein. The method 1000 begins at 1002, in which respective input electrical signals are received via a plurality of input channels (e.g., channels 102), as sensed by a set of electrodes (e.g., electrodes 202, 402, 404). At 1004, the input signals are filtered (e.g., by filter 104, 204 or 408). For example, the filtering (e.g., low-pass, anti-aliasing) provides corresponding filtered signals that retain power line interference signals as a common mode signal. The filtered signals may be provided as inputs to respective differential amplifiers.

At 1006, respective pairs of the input signals (e.g., filtered signals) are amplified via a plurality of differential amplifiers. Thus, an amplified output signal is provided corresponding to the difference a difference between respective pairs of the input electrical signals. At 1008, the amplified output signals are analyzed (e.g., by logic 110, 430 and 500) to determine a relative impedance associated with each electrode in the set of electrodes. For example, when the amplified signal is generated for an electrode pair that each has good contact, the amplified output signal will approximate zero (e.g., demonstrating good common mode rejection performance). In examples when the amplified signal is generated for an electrode pair that each does not have good contact, the amplified output signal will have a non-zero amplitude (e.g., demonstrating poor common mode rejection performance). The common mode rejection performance may thus be used as a metric to determine relative impedance for the input channels.

In some examples, the analysis at 1008 may include a signal processing method. The signal processing may include converting the amplified output signals of each of the plurality of differential amplifiers to frequency domain data having an amplitude representing signal power at different frequencies. This may include a range of frequencies retained following the filtering at 1004. The analysis may also include applying a threshold to the frequency domain data at a predetermined frequency corresponding to the common mode signal. With such signal processing, the channel data thus may be generated based on the application of the threshold to the frequency domain data.

Additionally or alternatively, in some examples, the electrodes and associated input channels are arranged in a plurality of spatial zones that each include a proper subset of the input electrical signals. A zonal threshold may be calculated for each of the plurality of spatial zones and each zonal threshold applied to the frequency domain data corresponding to a respective zone. In this way, channel integrity detection and associated analysis may be implemented spatially for the subsets of signals originating from each spatial zone.

At 1010, channel data (e.g., data 112, 434 and 516) is generated to specify an acceptability or unacceptability for each of the plurality of input channels based on the analyzing. The channel data may be stored in memory for subsequent processing. For example, at 1012, an output may be provided. The output may be a visualization (e.g., graphical output) representing the acceptability of the channels, such as a channel map simulating the arrangement of electrodes positioned on the body surface. In other example, the output may include a map of the acquired signals, such a body surface map or a map derived by inverse reconstruction onto a surface within the patient's body.

Additionally or alternatively, the respective input electrical signals that are received at 1002 may include a reference signal and a plurality of other electrical signals. In examples where the reference signal exists (e.g., in many high-density electrode systems), each of the plurality of differential amplifiers may receive the reference signal at one input thereof and one of the plurality of other electrical signals at another input thereof. As a result, each of the plurality of differential amplifiers provides the difference signal to indicate a common mode rejection between the reference signal and each of the other electrical signals.

Figure 11:
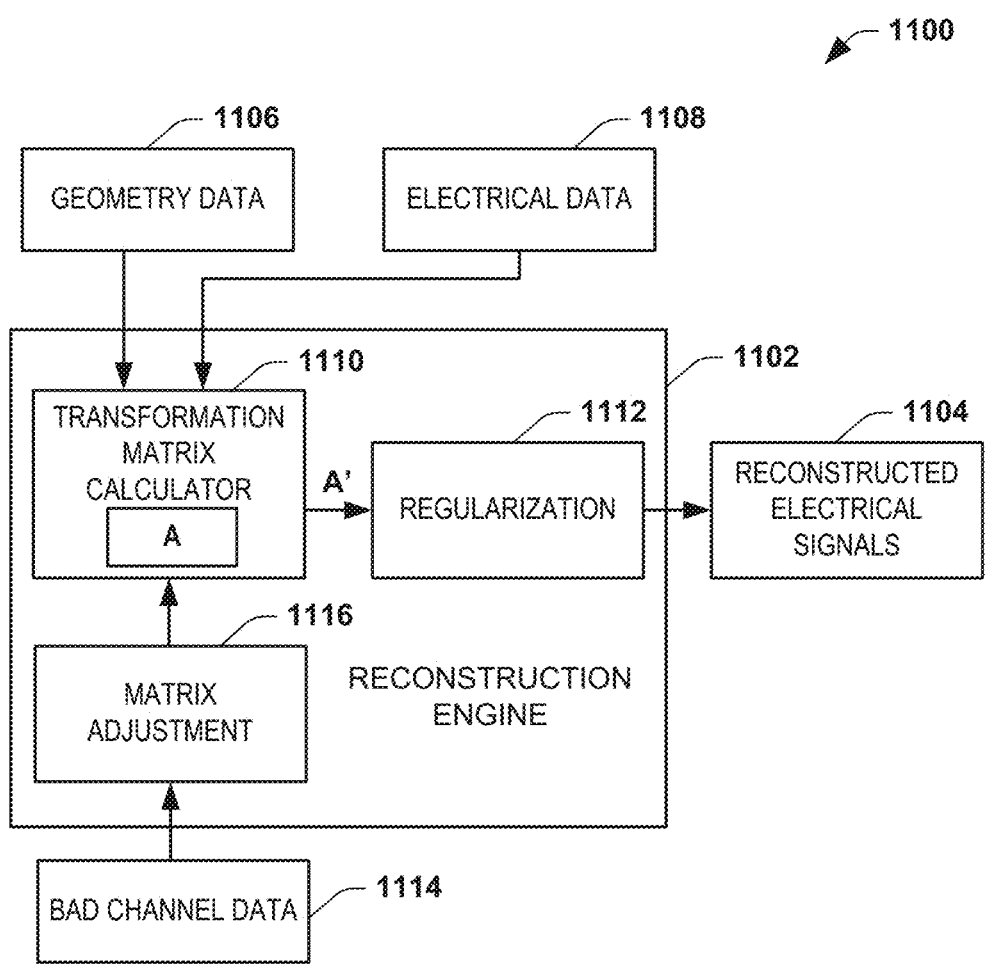
FIG. 11 depicts an example system to generate reconstructed electrical signals.

FIG. 11 depicts an example of a system 1100 to reconstruct electrical signals on a surface of interest (e.g., a surface envelope) based on electrical signals measured on a different surface (e.g., body surface) that is spaced apart from the surface of interest. The system 1100 includes a reconstruction engine 1102 that is programmed to reconstruct the electrical signal on the surface of interest based on geometry data 1106, electrical data 1108 and channel data 1114. For example, the reconstruction engine 1102 may be programmed to implement various methods as part of the solution of the inverse problem, such as including a boundary element method (BEM) or method of fundamental solution (MFS). Examples of approaches that the reconstruction engine may be programmed to implement to solve the inverse problem, including forward and inverse computations, are disclosed in U.S. Pat. Nos. 7,983,743 and 6,772,004, which are incorporated herein by reference.

The reconstruction engine 1102 can be programmed to implement an inverse method that includes a transformation matrix calculator 1110 and a regularization method 1112. The reconstruction engine 1102 further is configured to impose boundary condition on the computations implemented by the transformation matrix calculator, which may include or be derived from the geometry data 1106 and the electrical data 1108. The values for each unit of the boundary condition being imposed can include fixed or variable boundary condition parameters, such as may further vary based on the channel data 1114.

For example, the channel data 1114 may specify one or more bad input channels, such as corresponding to condition where an electrode is not connected to the target or is otherwise an unacceptable connection. In some examples the channel data may be generated according to systems and methods disclosed herein with respect to FIGS. 1-10. In other examples, alternative approaches may be utilized to generate the channel data 1114 to provide a measure of channel integrity including to identify bad channels. An example of one such alternative approach is disclosed in U.S. Pat. No. 9,470,728, which is incorporated herein by reference.

As a further example, the geometry data 1106 can identify a three-dimensional spatial position location of the sensing electrodes (also referred to sensing nodes) in a respective coordinate system. For example the geometry data 1106 can include a list of nodes, and the position for each node, such as can be produced by segmenting imaging data that has been acquired by an appropriate imaging modality. Examples of imaging modalities include ultrasound, computed tomography (CT), 3D Rotational angiography (3DRA), magnetic resonance imaging (MRI), x-ray, positron emission tomography (PET), fluoroscopy, and the like. Such imaging can be performed separately (e.g., before or after) the measurements utilized to generate the electrical data 1108. Alternatively, imaging may be performed concurrently with recording the electrical activity that is utilized to generate the patient electrical data 1108. The geometry data 1106 can also include coordinates (e.g., in three-dimensional space) for each of the nodes. In other examples, the geometry data 1106 can be acquired by manual measurements between electrodes or other means (e.g., a digitizer).

As another example, the geometry data 1106 can correspond to a mathematical model of a torso that has been constructed based on image data for the patient's organ. A generic (non-patient) model can also be utilized to provide the geometry data 1106. The generic model further may be customized (e.g., deformed) for a given patient, such as based on patient characteristics include size image data, health conditions or the like. Appropriate anatomical or other landmarks, including locations for the electrodes can also be represented in the geometry data 1106, such as by performing segmentation of the imaging data. The identification of such landmarks can be done manually (e.g., by a person via image editing software) or automatically (e.g., via image processing techniques).

The electrical data 1108 can represent body surface electrical measurements acquired by an arrangement of sensing electrodes over one or more time intervals. The body surface electrical data 1108, for example, can include measured electrical signals (e.g., surface potentials) obtained from a plurality of sensing electrodes distributed across the body surface of a patient. Similar to other examples disclosed herein, the distribution of electrodes can cover substantially the entire thorax of a patient or the sensing electrodes can be distributed across a predetermined section of the body surface such as configured for detecting electrical signals predetermined as being sufficient to detect electrical information corresponding to a predetermined region of interest for the patient's body. In other examples, a set of electrodes can be preconfigured to cover a selected region of the patient's torso for monitoring atrial electrical activity of one or both atrium of a patient's heart, such as for studying atrial fibrillation. In other examples other preconfigured sets of electrodes can be utilized according to application requirements, which can include invasive and non-invasive measurements. The body surface electrical data 1108 thus can be stored in memory that resides in or is accessible by a computer implementing the reconstruction engine 1102.

The transformation matrix calculator 1110 is thus programmed to compute a transformation matrix, such as demonstrated at A, based on at least one boundary condition and the geometry data 1106. The transformation matrix A may be computed a priori or in real time during signal acquisition that provides the electrical data 1108. The transformation matrix may include one or more submatrices, which may depend on the type of inverse reconstruction being implemented by the reconstruction engine 1102.

The reconstruction engine 1102 includes a matrix adjustment method 1116 programmed to modify the transformation matrix based on the channel data to provide a modified transformation matrix. For example, the matrix adjustment method 1116 modifies the transformation matrix to ignore channel information (e.g., values of electrical signals) captured by bad electrodes, while still retaining the spatial information (e.g., geometry data) associated with such bad electrodes.

The regularization method 1112 is programmed to estimate the reconstructed electrical signals on the envelope based on the modified transformation matrix A' and the electrical signals from the set of electrodes (e.g., in the electrical data 1108). As an example, the regularization method 1112 can be programmed to implement Tikhonov regularization, such as described in the above-incorporated U.S. Pat. No. 6,772,004. Other regularization techniques may be used, including generalized minimum residual (GMRes) regularization, such as disclosed in U.S. Pat. No. 7,016,719, which was filed Oct. 4, 2002, and is incorporated herein by reference. The reconstruction engine 1102 can in turn provide the reconstructed electrical signals 1104 based on the regularized matrix. The reconstructed electrical signals 1104 thus represent electrical signals on a cardiac envelope within the body based on the electrical data that is acquired non-invasively using body surface electrodes.

By way of further example where the transformation matrix calculator 1110 of the reconstruction engine 1102 uses BEM (boundary element method), boundary condition data may be employed to produce a linear system that is constrained by each one or more boundary conditions that is applied. The matrix adjustment method converts channel signal information in the transformation matrix for each bad channel, which is identified in the channel data 1114, to unknown variables in the modified transformation matrix. The regularization method 1112 can apply a regularization technique to solve the unknown values of electrical signals on the envelope of interest from the transformation matrix computed by the calculator 1110. The regularization method 1112 is further programmed to solve for the unknown variables, which had been inserted into the transformation matrix (by matrix adjustment method), as part of the estimation of reconstructed electrical signals on the cardiac envelope. That is, a matrix adjustment 1116 modifies the transformation matrix by replacing sensor signal information for each identified bad channel with unknown values (parameters), which are solved by the regularization method 1112.

In some examples, the reconstruction engine 1102 further can implement an inverse method that is programmed to meshlessly compute an estimate of reconstructed electrical activity using the MFS by imposing boundary conditions to constrain certain computations, namely determining coefficients of the transformation matrix A. As an example, the reconstruction engine can be implemented meshlessly by imposing boundary conditions determined from the electrical data and the geometry, such as according to the technique disclosed in U.S. Pat. No. 7,983,743, which is incorporated herein by reference.

For the example where the reconstruction engine 1102 uses the MFS to solve the inverse problem and compute the reconstructed electrical signals 1104 on the cardiac envelope, the inverse reconstruction constitutes a Cauchy problem for Laplace's equation:

$$\nabla^2 u(x) = 0, x \in \Omega$$

$$u(x) = a_0 + \Sigma_i a_i f(x - y_i)$$

The MFS thus utilizes boundary conditions on the torso surface:
Dirichlet boundary condition: $u(x) = u_T(x)$, $x \in \Gamma_T$
Neumann boundary condition:

$$\frac{du(x)}{d\vec{n}} = c_T(x) = 0, x \in \Gamma_T$$

where $\Omega$ is the 3D volume domain between the heart's epicardial surface and the torso surface $\Gamma_T$ That is, the boundary conditions for that include a first boundary condition (e.g., the Dirichlet boundary condition) that parameterizes signal channel information for the set of electrodes and a second boundary condition (e.g., the Neumann boundary condition) that parameterizes the spatial geometry of the set of electrodes. In this example, the matrix adjustment method 1116 is programmed to remove the signal channel information from the first boundary condition (Dirichlet boundary condition) for each bad channel that is identified in the channel data 1114, while retaining the spatial geometry for the entire set of electrodes regardless of the indication of acceptability of each of the plurality of input channels.

As an example, FIG. 13 depicts a transformation matrix 1300 that may be computed when implementing inverse reconstruction according to MFS. The transformation matrix includes Dirichlet boundary conditions describing channel information for electrical signals sensed across the body surface demonstrated at 1302. The transformation matrix 1300 also includes Neumann boundary conditions on the torso surface corresponding to spatial geometry information associated with the electrodes on the torso surface, demonstrated at 1304. For purposes of this example, channel information for a given row of the matrix 1300, which represents the Dirichlet boundary condition associated with a given channel, is illustrated as being crossed out to demonstrate that it has been removed (by matrix adjustment method 1116) from the Dirichlet boundary condition 1302, and thus being ignored (not utilized) in the adjusted transformation matrix 1300. The regularization method 1112 thus estimates the value of the inverse of the transformation matrix (e.g., $[=A^{-1}*V_T]$) using a regularization technique such as, Tikhonov zero order regularization or the GMRes method. The reconstruction engine 1102 in turn computes values of electrical activity on the cardiac envelope of interest (e.g., epicardial cardiac surface potentials) node location (e.g., as disclosed in the above-incorporated U.S. Pat. No. 7,983,743).

Figure 12:
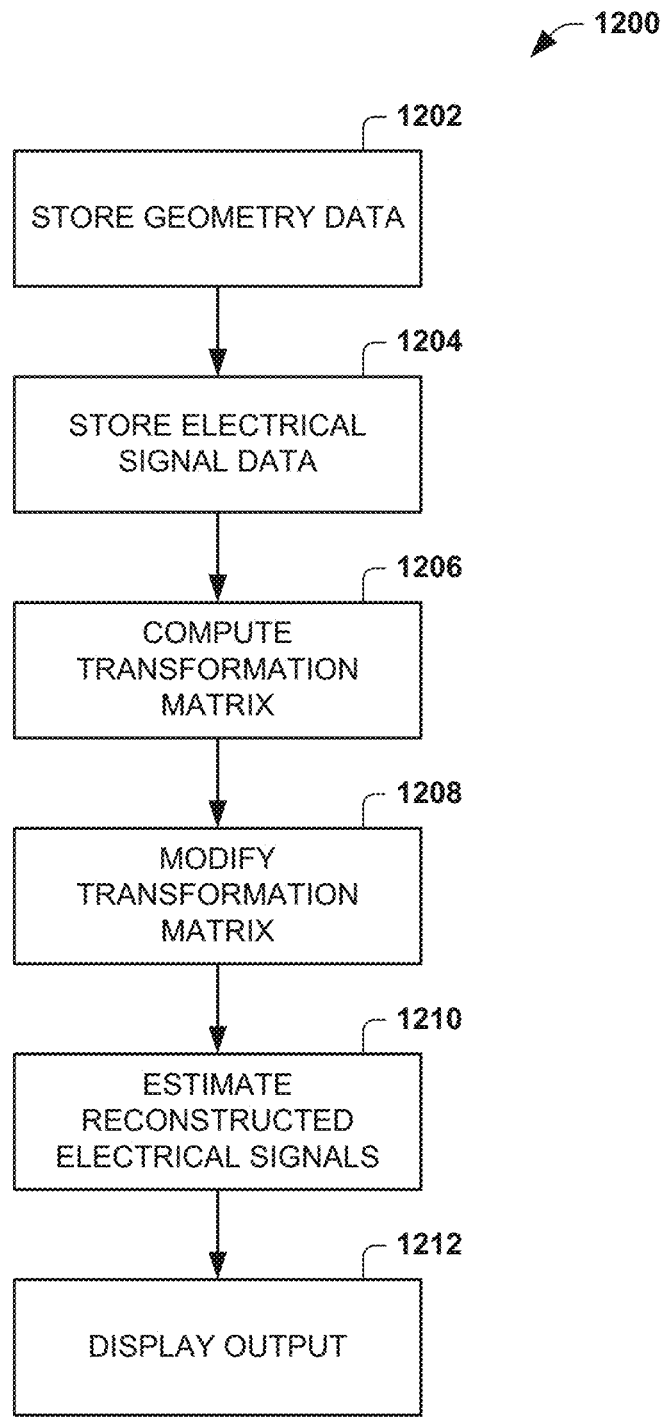
FIG. 12 is a flow diagram depicting an example of a method for generating reconstructed electrical signals.

FIG. 12 is a flow diagram depicting an example of a method 1200 for generating reconstructed electrical signals. The method 1200 includes storing geometry data at 1202 and storing electrical signal data at 1204. The electrical data includes electrical signals measured by a plurality of electrodes arranged for sensing body surface electrical activity. At 1206, a transformation matrix is computed (e.g., by matrix calculator 1110) based on at least one boundary condition and geometry data associated with the electrodes. At 1208, the transformation matrix is modified (e.g., by matrix adjustment method) based on bad channel data to a modified transformation matrix. The bad channel data specifies that a connection of one or more of the electrodes with the body surface is unacceptable. The matrix can be modified to ignore or remove from the matrix the contribution of signal information for each bad channel that is identified, while retaining location information for each of the plurality of channels (including bad channel). At 1210, the reconstructed electrical signals on the cardiac envelope are estimated based on the modified transformation matrix and the electrical signals from the plurality of electrodes. A visualization representing a graphical map of the reconstructed electrical signals on the cardiac envelope may be generated.

In some examples, the method 1200 implements the MFS to perform the inverse reconstruction that provides the reconstructed electrical signals. As part of the MFS, the transformation matrix includes a first boundary condition (e.g., the Dirichlet condition) that parameterizes signal channel information for the set of electrodes and a second boundary condition (e.g., the Neumann condition) that parameterizes the spatial geometry of the plurality of electrodes. The matrix modification at 1208 thus may include removing the signal channel information from the first boundary condition for each bad channel that is identified while not changing the second boundary condition, regardless of the indication of acceptability of each of the plurality of input channels.

In another example, the method 1200 implements a boundary element method to compute the reconstructed electrical signals on the cardiac envelope. In this example, the matrix modification at 1208 further includes converting channel signal information in the transformation matrix for each bad channel that is identified to an unknown parameter for a corresponding body surface signal. The estimation of reconstructed electrical signals includes solving for each of the unknown parameters, which correspond to signal information for the bad channels.

As a further example, the bad channel data may be determined according to the systems and methods disclosed herein (see, e.g., FIG. 10). Briefly stated, respective input electrical signals can be sensed by the plurality of electrodes and received via corresponding input channels. A difference between respective pairs of the input electrical signals can be amplified (e.g., by differential amplifiers) to provide an amplified output signal corresponding to the difference. The amplified output signals are further analyzed to determine a relative impedance associated with each electrode in the set of electrodes, such as based on the common mode rejection performance of the each amplifier. The bad channel data may be generated based on the analysis of the amplifier outputs, such.

FIGS. 14A and 14B depict examples of graphical maps 1402 and 1404 that can be generated from reconstructed electrical signals for a normal sinus rhythm. The example map 1402 in FIG. 14A is generated using an existing approach to detect the channels in which the electrical information for each bad channel is interpolated from its neighboring electrodes. As demonstrated in FIG. 14A, a region of the graphical map results in artifacts 1408 on the resulting map 1402. By contrast, the graphical map 1404 is generated using reconstruction method disclosed herein, in which signal information from bad channels has been ignored, and results in a graphical map that does not exhibit the artifacts.

Figure 15A:
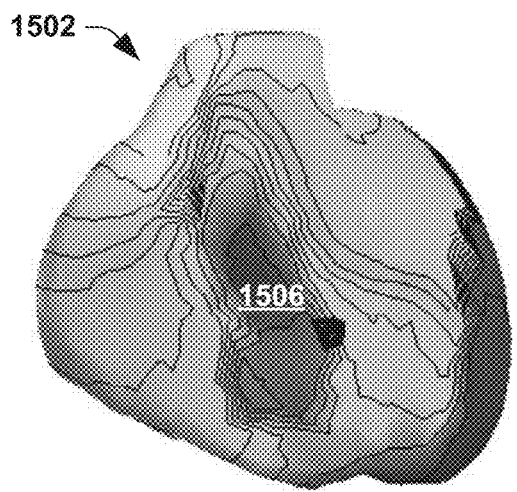
FIGS. 15A and 15B depict examples of graphical maps electrical signals for a premature ventricular contraction reconstructed with and without including signal information for bad channels.
Figure 15B:
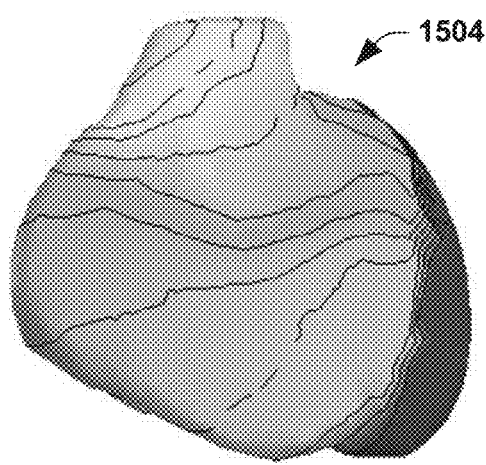

FIGS. 15A and 15B depict examples of graphical maps 1502 and 1504 of reconstructed electrical signals for a premature ventricular contraction. In this example, the graphical map 1502 is generated according to an existing approach in which signal information is interpolated for bad electrodes according to the electrical information of its neighboring electrodes. As a result, artifacts demonstrated at 1506 occur in the graphical map 1502. The other graphical map 1504, however, does not exhibit such artifacts as it is reconstructed based on this disclosure in which signal information for bad channels is ignored while the geometry information for such bad channels is retained as part of the inverse reconstruction method.

Figure 16:
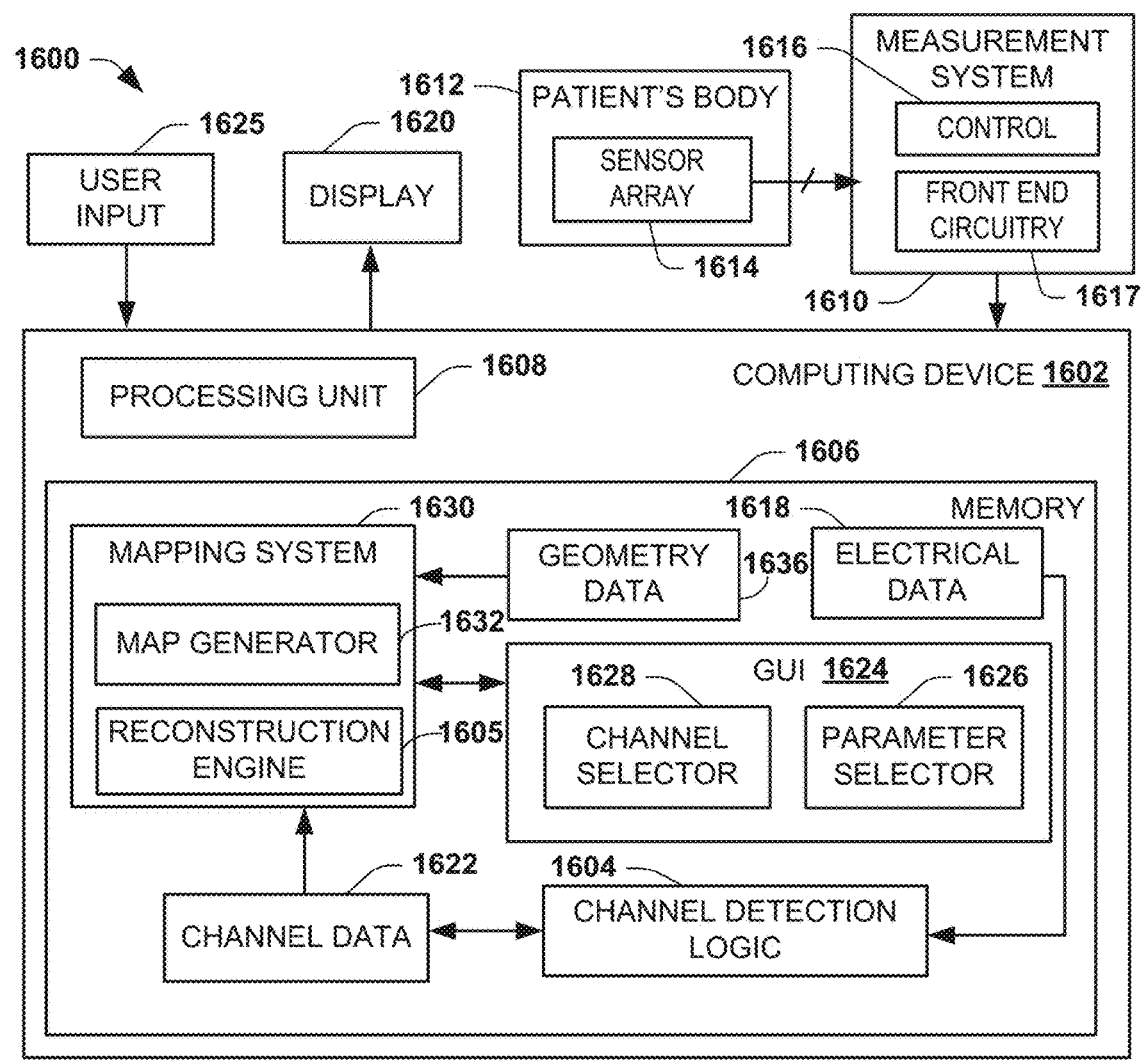
FIG. 16 depicts an example of a system for generating graphical outputs based on electrophysiological signals measured from a patient's body.

FIG. 16 depicts an example of a system 1600 for generating graphical outputs based on electrophysiological signals measured from a patient's body. In some examples, the sensed electrical activity can be used to generate one or more graphical representations (e.g., graphical maps of electroanatomic activity) based on the sensed electrical activity, such as for a region of patient anatomy. The system 1600 includes a computing device 1602. As an example, the computing device 1602 can be implemented as a laptop computer, a desktop computer, a server, a tablet computer, a workstation or the like. The computing device 1602 can include memory 1606 for storing data and machine-readable instructions. The memory 1606 can be implemented, for example, as a non-transitory computer storage medium, such as volatile memory (e.g., random access memory), non-volatile memory (e.g., a hard disk drive, a solid-state drive, flash memory or the like) or a combination thereof.

The computing device 1602 can also include a processing unit 1608 to access the memory 1606 and execute the machine-readable instructions stored in the memory. The processing unit 1608 could be implemented, for example, as one or more processor cores. In the present examples, although the components of the computing device 1602 are illustrated as being implemented on the same system, in other examples, the different components could be distributed across different systems and communicate, for example, over a network.

The instructions, which may be executed by the processing unit 1608 include channel detection logic 1604 and/or a reconstruction engine 1605. The channel detection logic 1604 may correspond to logic 110, 430 as well as instructions programmed to execute portions of the method 1000, as disclosed herein. The reconstruction engine 1605 may correspond to reconstruction engine 1102 as well as instructions programmed to execute portions of the method 1200 disclosed herein. Accordingly, references may be made to earlier portions of this document for additional information about these the channel detection logic 1604 and reconstruction engine 1605.

The system 1600 can include a measurement system 1610 to acquire electrophysiology information for a patient 1612. In the example of FIG. 16, a sensor array 1614 includes one or more electrodes that can be utilized for recording patient electrical activity. As one example, the sensor array 1614 can correspond to an arrangement of body surface electrodes that are distributed over and around the patient's thorax for measuring electrical activity associated with the patient's heart (e.g., as part of an electrophysiology procedure). In some examples, there can be about 200 or more sensors (e.g., about 252 sensors) in the array 1614, each electrode corresponding to a node that defines a respective input channel. Various examples of a non-invasive sensor array are disclosed herein. Additionally or alternatively, the one or more invasive electrodes (e.g., for sensing or therapy delivery) can be inserted into the patient's body 1612.

The measurement system 1610 receives sensed electrical signals from the electrodes in the corresponding sensor array 1614. The measurement system 1610 can include appropriate controls 1616 and front end circuitry 1617 for providing corresponding electrical data 1618. The front end circuitry 1617 can include an arrangement of filters, amplifiers and ADCs for each respective channel, such as disclosed with respect to FIGS. 1-4. The electrical data 1618 thus may include digitized amplified outputs from differential amplifiers (e.g., 108, 208 or 408), such as corresponding to common mode signal rejection signals, as disclosed herein. Additionally, the electrical data 1618 includes signal information that describes electrical activity sensed for each of a plurality of input channels detected by the sensors in the sensor array 1614, which signal information may have power line noise filtered out.

The electrical data 1618 can be stored in the memory 1606 as analog or digital information. Appropriate time stamps and channel identifiers can be utilized for indexing the respective electrical data 1618 to facilitate the evaluation and analysis thereof. As an example, each of the sensor electrodes in the sensor array 1614 can simultaneously sense body surface electrical activity and provide corresponding electrical data 1618 for one or more user selected time intervals.

The device 1602 includes instructions in the memory configured to process the electrical data 1618 and to generate one or more outputs. The output can be stored in the memory 1606 and provided to a display 1620 or other type of output device. As disclosed herein, the type of output and information presented can vary depending on, for example, application requirements of the user.

As mentioned, the computing device 1602 is programmed to employ channel detection methods 1604 to improve the accuracy in associated processing and analysis performed by the reconstruction engine 1605. The channel detection logic 1604 can, for example, be implemented to perform any combination of the channel analysis and detection functions and methods disclosed herein (see, e.g., FIGS. 1, 4, 5 and 10 and the corresponding description). The channel detection 1604 thus can provide channel data 1622 specifying which input channels are bad (or good) based on signal processing on the electrical data 1618. The resulting channel integrity data 1622 provided by the detection logic 1604 can be stored in the memory 1606, separately or in conjunction with the electrical data 1618. In this way, bad channels can be tagged for further processing and analysis.

In some examples, the channel detection 1604 can interface with a graphical user interface (GUI) 1624 stored as executable instructions in the memory 1606. The GUI 1624 thus can provide an interactive user interface, such that the thresholds and related parameters utilized by the channel detection 1604 can be set in response to a user input 1625. The GUI 1624 can provide data that can be rendered as interactive graphics on the display 1620. For example, the GUI 1624 can generate an interactive graphical representation that differentiates between good and bad channels (e.g., a graphical representation of the sensor array 1614 differentiating graphically or otherwise between bad and good channels).

In the example of FIG. 16, the GUI 1624 includes a parameter selector 1626 that can be employed to program parameters (e.g., thresholds, constraints, data sources and the like) utilized by the channel detection 1604 and. In some examples, default values can be utilized unless modified in response to a user input, such as disclosed herein.

The GUI 1624 can also include a channel selector 1628 programmed to select and deselect channels in response to a user input. The channel selector 1628 can be employed to manually include or exclude selected channels, which may override bad channel information determined by the channel detection logic 1604. For instance, the GUI 1624 can indicate (e.g., by graphical and/or textual indicators) on the display 1620 which channels are bad channels and/or a set of channels considered to be high integrity (e.g., good) channels. A user can thus employ the channel selector 1628 of the GUI 1624 to include an identified bad channel that has or exclude a good channel.

As a further example, the computing device 1602 can include a mapping system 1630 that is programmed to generate electroanatomical map based on the electrical data 1618, namely based on the electrical data for the channels.

In some examples, the mapping system 1630 includes a reconstruction engine 1605 programmed to reconstruct heart electrical activity by combining the electrical data 1618 with geometry data 1636 through an inverse calculation. The geometry data may be generated as disclosed herein, such as including patient-specific geometry, a generic geometry information or any combination thereof. The reconstruction engine is programmed to implement an inverse method, such as disclosed herein with respect to FIG. 11. For instance, the reconstruction engine employs a transformation matrix (e.g., computed by matrix calculator 110) and a regularization method (e.g., method 1112) to reconstruct the electrical activity sensed by the sensor array 1614 on the patient's body onto an anatomic envelope, such as an epicardial surface, an endocardial surface or other envelope. The reconstruction engine 1605 further may modify the transformation matrix based on the channel data, as disclosed herein.

The mapping system 1630 can also include a map generator 1632 that is programmed to generate map data representing a graphical (e.g., an electrical or electroanatomic map) based on the electrical data 1618. The map generator 1632 can generate the map data to visualize a graphical map via the display 1620, which is spatially superimposed on a graphical representation of an anatomical structure (e.g., the body surface or the heart). In some examples, such as in response to the user input 1625, the map generator 1632 can employ the reconstructed electrical data computed via the inverse method to produce corresponding map of electrical activity. The map can represent electrical activity of the patient's heart on the display 1620, such as corresponding to a map of reconstructed electrograms (e.g., a potential map). Alternatively or additionally, the computing device 1602 can compute other electrical characteristics from the reconstructed electrograms, such as an activation map, a repolarization map, a propagation map or other electrical characteristic that can be computed from the measurement data. The type of map can be set in response to the user input 1625 via the GUI 1624.

In view of the foregoing, an automatic bad channel detection method has been disclosed to improve accuracy and user experience. The approach disclosed herein thus can enhance the user interaction and increase the ease of beat-by-beat analysis. The bad channel detection methods and systems can be implemented to identify and adjust subsequent signal processing methods (e.g., inverse algorithms).

As will be appreciated by those skilled in the art, portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims.

As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
   a plurality of input channels, each of the input channels having a respective input coupled to a respective one of a plurality of electrodes and comprising:
      a filter having an input and an output, the input coupled to a respective channel input, and the filter configured to filter an electrical signal representative of an electrophysiological signals measured by a respective electrode of the respective channel and remove signal components outside a frequency range of a common mode signal;
      a differential amplifier having a pair of inputs coupled to a pair of respective filter outputs to receive a respective pair of filtered electrical signals, the differential amplifier configured to provide an amplifier output signal based on a difference between the pair of electrical signals;
   one or more non-transitory computer-readable media comprising data and machine readable instructions executable by a processor, the data comprising processed electrical signal data representative of filtered and differentially amplified signals provided by the respective differential amplifiers from respective of electrodes, and the machine readable instructions comprising:
   channel detection logic programmed to:
      generate frequency domain data having an amplitude value representing a level of common mode rejection at different frequencies based on the processed electrical signal data; and
      apply a threshold to the frequency domain data at a frequency, corresponding to a frequency of the common mode signal of the respective differential amplifiers, to provide channel data indicating an acceptability or unacceptability of the received electrical signals for each of the respective input channels.

2. The system of claim 1, wherein the channel detection logic is programmed to generate the frequency domain data by applying a fast Fourier transform (FFT) to the processed electrical signal data to convert the amplifier output signals to the frequency domain data.

3. The system of claim 1, wherein the machine readable instructions further comprise:
   a reconstruction engine programmed to reconstruct electrical signals on a cardiac envelope based on the channel data, the electrical signals from the respective electrodes and geometry data representing a spatial geometry of the respective electrodes; and
   an output generator programmed to generate a visualization representing the reconstructed electrical signals on the cardiac envelope.

4. The system of claim 3, wherein the visualization generated by the output generator is a graphical output that displays the reconstructed electrical signals on the cardiac envelope, the output generator being programmed to cause the graphical output to be rendered on a display.

5. The system of claim 3, wherein the reconstruction engine further comprises:
   a matrix calculator programmed to compute a transformation matrix based on at least one boundary condition and the geometry data of the respective electrodes;
   a matrix adjustment method programmed to modify the transformation matrix based on the channel data indicating the acceptability of each of the received electrical signals to provide a modified transformation matrix; and
   a regularization method programmed to estimate the reconstructed electrical signals on the cardiac envelope based on the modified transformation matrix and the electrical signals from the respective electrodes.

6. The system of claim 5,
   wherein the reconstruction engine is programmed to implement a method of fundamental solution to compute the reconstructed electrical signals on the cardiac envelope,
   wherein the transformation matrix includes a first boundary condition that parameterizes signal channel information for the respective electrodes and a second boundary condition that parameterizes the spatial geometry of the respective electrodes, and
   wherein the matrix adjustment method is programmed to remove the signal channel information from the first boundary condition for each bad channel that is identified in the acceptability of the respective received electrical signals while retaining the spatial geometry for the respective electrodes regardless of the acceptability of the received electrical signals indicated by the channel data.

7. The system of claim 5,
wherein the reconstruction engine is programmed to implement a boundary element method to compute the reconstructed electrical signals on the cardiac envelope, and
wherein the matrix adjustment method is programmed to convert channel signal information in the transformation matrix for each bad channel, which is identified in the channel data of the respective received electrical signals, to unknown variables for the regularization method to solve as part of the estimation of reconstructed electrical signals on the cardiac envelope.

8. The system of claim 1, wherein the respective electrodes includes a reference electrode and other electrodes, each respective pair of the electrical signals includes a signal from the reference electrode and one of the other electrodes.

9. The system of claim 8, wherein the filters are configured to filter the electrical signals and provide filtered electrical signals at the inputs of the differential amplifiers, in which each of the filtered electrical signals include signal components in the frequency range of the common mode signal.

10. The system of claim 9, wherein the filtered electrical signals provided at the inputs of the differential amplifiers include power line interference signals corresponding to the common mode signal of each differential amplifier.

11. The system of claim 1, wherein the respective electrodes are arranged in spatial zones that each includes a proper subset of the electrical signals, wherein the channel detection logic is programmed to:
calculate a zonal threshold for each of the spatial zones; and
apply each zonal threshold for a respective zone to the frequency domain data associated with the respective zone to implement analysis spatially for signals originating from each spatial zone to provide the channel data.

12. A system comprising:
filters configured to filter electrophysiological signals measured by a plurality of respective electrodes and provide filtered electrophysiological signals, in which each of the filtered electrophysiological signals includes signal components in the frequency range of a common mode signal;
an amplifier circuit comprising a plurality of differential amplifiers, in which each differential amplifier has inputs to receive a pair of the respective filtered electrophysiological signals associated with respective input channels, each differential amplifier configured to provide a respective amplifier output signal based on a difference between the pair of electrical signals received by the respective differential amplifier;
an analog-to-digital converter circuit configured to convert the amplifier output signals to processed electrical signal data representative of the respective amplifier output signals provided by differential amplifiers;
memory comprising machine readable instructions and data, the data comprising the processed electrical signal data;
one or more processors to access the memory and execute the machine readable instructions, the machine readable instructions comprising:

signal processing code programmed to convert the processed electrical signal data to frequency domain data having an amplitude value representing a level of common mode rejection at different frequencies for each of the respective input channels;
channel detection logic programmed to provide channel data indicative of an acceptability of respective electrical signals for each of the respective input channels in response to applying a threshold to the frequency domain data at a frequency, corresponding to a frequency of the common mode signal of each of the differential amplifiers; and
a reconstruction engine programmed to reconstruct electrical signals on a cardiac envelope based on the electrophysiological signals from an acceptable set of the electrodes, and geometry data representing a spatial geometry of the respective electrodes and the cardiac envelope, in which the acceptable set of the electrodes is determined based on the channel data.

13. The system of claim 12, wherein the machine readable instructions further comprise an output generator programmed to generate a visualization representing the reconstructed electrical signals on the cardiac envelope.

14. The system of claim 13, wherein the channel detection logic is programmed to apply a fast Fourier transform (FFT) to the processed electrical signal data to convert the amplifier output signals to provide the frequency domain data.

15. The system of claim 14, wherein the reconstruction engine comprises:
a matrix calculator programmed to compute a transformation matrix based on at least one boundary condition and the geometry data of the respective electrodes;
a matrix adjustment method programmed to modify the transformation matrix based on the channel data indicating the acceptability of the received electrical signals to provide a modified transformation matrix; and
a regularization method programmed to estimate the reconstructed electrical signals on the cardiac envelope based on the modified transformation matrix and the electrical signals from the respective electrodes.

16. The system of claim 15,
wherein the reconstruction engine is programmed to implement a method of fundamental solution to compute the reconstructed electrical signals on the cardiac envelope,
wherein the transformation matrix includes a first boundary condition that parameterizes signal channel information for the respective electrodes and a second boundary condition that parameterizes the spatial geometry of the respective electrodes, and
wherein the matrix adjustment method is programmed to remove the signal channel information from the first boundary condition for respective bad channels identified in the acceptability of the electrical signals while retaining the spatial geometry for the respective electrodes regardless of the acceptability of the electrical signals indicated by the channel data.

17. The system of claim 16,
wherein the reconstruction engine is programmed to implement a boundary element method to compute the reconstructed electrical signals on the cardiac envelope, and
wherein the matrix adjustment method is programmed to convert channel signal information in the transformation matrix for a respective bad channel, which is identified in the channel data, to unknown variables for the regularization method to solve as part of the estimation of reconstructed electrical signals on the cardiac envelope.

18. The system of claim 15, wherein the respective electrodes are arranged in spatial zones that each includes a proper subset of the electrical signals, wherein the channel detection logic is further programmed to:
   calculate a zonal threshold for the respective spatial zones;
   apply the zonal threshold for a respective zone to the frequency and domain data for the respective spatial zone to implement analysis spatially and to provide the channel data.

19. The system of claim 12, wherein the respective electrodes includes a reference electrode and other electrodes, each respective pair of the electrical signals includes a signal from the reference electrode and one of the other electrodes, and wherein the filtered electrophysiological signals have a frequency below a frequency threshold, and thus include the frequency of the common mode signal.

20. The system of claim 19, wherein the filtered electrophysiological signals provided to the inputs of the differential amplifiers include power line interference signals corresponding to the common mode signal of the respective differential amplifiers.

* * * * *